United States Patent

Suzuki et al.

Patent Number: 5,281,610
Date of Patent: Jan. 25, 1994

[54] CONDENSED NAPHTHYRIDINE DERIVATIVES

[75] Inventors: Fumio Suzuki, Mishima; Takashi Kawakita, Shizuoka; Takeshi Kuroda, Ibaraki; Kenji Ohmori, Mishima; Hiroshi Nakajima, Shizuoka; Toshikazu Kamiya; Tatsuya Tamaoki, both of Machida, all of Japan

[73] Assignee: Kyowa Hakko Kogyo Co., Ltd., Tokyo, Japan

[21] Appl. No.: 993,920

[22] Filed: Dec. 18, 1992

Related U.S. Application Data

[63] Continuation of Ser. No. 921,720, Jul. 30, 1992, abandoned.

Foreign Application Priority Data

Jul. 31, 1991 [JP] Japan .................. 3-191909

[51] Int. Cl.$^5$ ................... A61K 31/435; C07D 471/22
[52] U.S. Cl. ...................... 514/293; 514/880; 546/82
[58] Field of Search ........ 546/82; 514/293, DIG. 880

[56] References Cited

U.S. PATENT DOCUMENTS 3,890,324 6/1975 Katner .................. 546/82
4,996,212 2/1991 Duelfer et al. ............ 546/82
5,010,084 4/1991 Suzuki et al. ............. 546/82

FOREIGN PATENT DOCUMENTS 0459505 12/1991 European Pat. Off.
0476544  3/1992 European Pat. Off.

OTHER PUBLICATIONS

Cecchi et al., Farm. Ed. Sc., vol. 42, No. 9 (1987) 671:80.

Primary Examiner—Marianne M. Cintins
Assistant Examiner—John Peabody
Attorney, Agent, or Firm—Fitzpatrick, Cella, Harper & Scinto

[57] ABSTRACT

Disclosed is a pyrazolonaphthyridine compound represented by the formula:

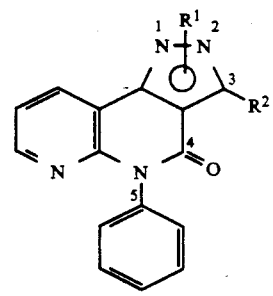

wherein $R^1$ is represents hydrogen, lower alkyl, aralkyl, or substituted or unsubstituted aryl, $R^2$ represents hydrogen, lower alkyl, thienyl, substituted or unsubsutituted aryl, hydroxy or amino, or a pharmaceutically acceptable salt thereof.

The compound possesses antiinflammatory effect, immunosuppressive effect, broncho-dilatory effect and hair growth-stimulative effect.

5 Claims, No Drawings

CONDENSED NAPHTHYRIDINE DERIVATIVES

This application is a continuation of application Ser. No. 921,720, filed Jul. 30, 1992, now abandoned.

BACKGROUND OF THE INVENTION

The present invention relates to novel 5-phenyl-pyrazolo naphthyridin-4-one derivatives having antiinflammatory effect, immunosuppressive effect, bronchodilatory effect and hair growth-stimulative effect.

The compounds represented by formula (A)

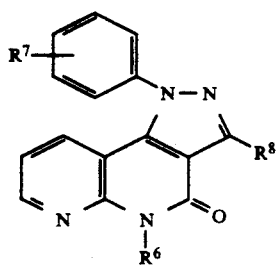

(A)

wherein $R^6$ is methyl, $R^8$ is phenyl and $R^7$ is 4-chloro, 3-chloro, 3-bromo or hydrogen, and the compounds represented by formula (A) wherein $R^6$ is methyl or benzyl, $R^8$ is methyl and $R^7$ is hydrogen, are disclosed [Farmaco. Ed. Sci., 42, 671, (1987)].

SUMMARY OF THE INVENTION

An object of the present invention is to provide a novel pyrazolonaphthyridine derivative having excellent anti-inflammatory effect, immunosuppressive effect, broncho-dilatory effect and hair growth-stimulative effect.

The present invention relates to a pyrazolonaphthyridine derivative represented by formula (I)

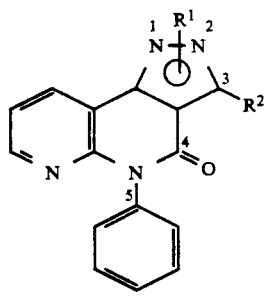

(I)

wherein $R^1$ represents hydrogen, lower alkyl, aralkyl, or substituted or unsubstituted aryl, $R^2$ represents hydrogen, lower alkyl, thienyl, substituted or unsubstituted aryl, hydroxy or amino, or a pharmaceutically acceptable salt thereof.

DETAILED DESCRIPTION OF THE INVENTION

The compound represented by formula (I) is referred to as Compound (I); and hereafter the same shall apply to other compounds of other formulae.

In the definition of various groups in formula (I), the lower alkyl includes, for example, straight or branched alkyl having 1 to 6 carbon atoms, such as methyl, ethyl, propyl, isopropyl, butyl, isobutyl, sec-butyl, tertbutyl, pentyl, neopentyl and hexyl. The aryl includes, for example, phenyl and naphthyl. The aralkyl are those having 7 to 15 carbon atoms, such as benzyl, phenethyl and benzhydryl. The aryl may be substituted by 1 to 3 substituents, and the substituent in the substituted aryl may be the same or different, and includes lower alkyl, lower alkoxy, hydroxy, amino, lower alkyl-substituted amino or halogen. The lower alkyl and the alkyl moiety in the lower alkoxy and lower alkyl-substituted amino have the same significance as defined above for alkyl. The halogen represents fluorine, chlorine, bromine and iodine.

As the pharmaceutically acceptable salts of Compound (I), mention may be made of pharmaceutically acceptable acid addition salts, for example, inorganic acid salts such as hydrochloride, sulfate and phosphate, and organic acid salts such as acetate, maleate, fumarate, tartrate and citrate.

Compound (I) wherein $R^1$ is hydrogen is usually present as a compound represented by formula (I-1) and/or a compound represented by formula (I-2). The relation between Compound (I-1) and Compound (I-2) is tautomer. Compound (I-1) and (I-2) are referred to as Compound (I-1) hereinafter.

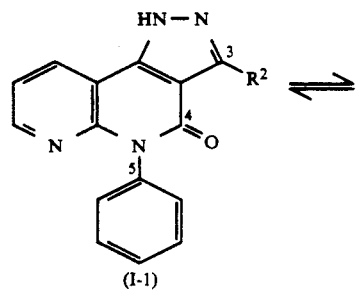

(I-1)

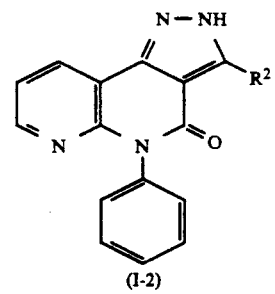

(I-2)

wherein $R^2$ is the same as defined above.

Process for producing Compound (I) is described below.

Process 1

Compound (Ia) which is Compound (I) wherein $R^1$ is the same as defined above and $R^2$ is hydrogen, lower alkyl, thienyl, or substituted or unsubstituted aryl may be obtained by the following reaction steps.

Step 1

-continued

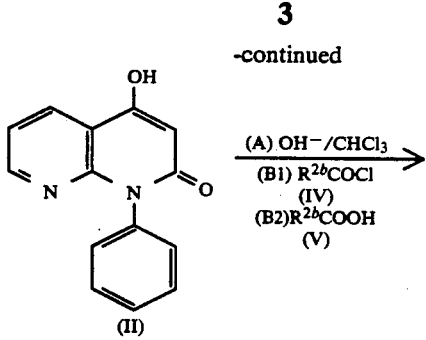

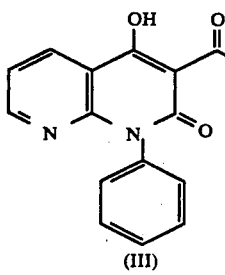

Step 2

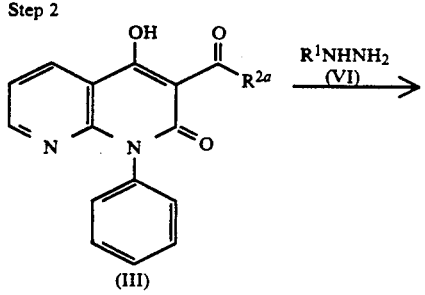

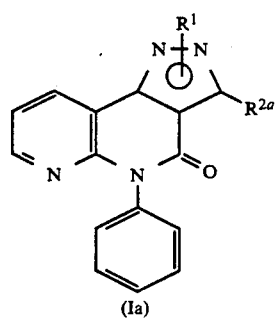

wherein R¹ is the same as defined above, $R^{2a}$ represents hydrogen, lower alkyl, thienyl or substituted or unsubstituted aryl, and $R^{2b}$ is the other groups than hydrogen for $R^{2a}$.

The starting Compound (II) can be synthesized by a known method, for example, the method described in Japanese Published Unexamined Patent Application No. 246183/1986.

Step 1

[A]: Compound (IIIa) which is Compound (III) wherein $R^{2a}$ is hydrogen may be obtained by reacting Compound (II) with chloroform in an aqueous solution of a strong alkali such as sodium hydroxide and potassium hydroxide.

[B1]: Compound (IIIb) which is Compound (III) wherein R² is lower alkyl, thienyl or substituted or unsubstituted aryl can be obtained by reacting Compound (II) with Compound (IV) in the presence of a Lewis acid.

Any reaction solvent can be used in the process so long as it is inert to the reaction. The reaction solvent includes, for example, aromatic hydrocarbons such as nitrobenzene and chlorobenzene, halogenated hydrocarbons such as 1,2-dichloroethane, dichloromethane, and chloroform, and carbon disulfide. The Lewis acid includes, for example, aluminum chloride, Tin (IV) chloride, titanium (IV) chloride, zinc chloride, and Iron (III) chloride. The reaction is completed in 5 minutes to 30 hours at 50° to 180° C.

[B2]: Compound (IIIb) may also be obtained by reacting Compound (II) with Compound (V) together with a dehydrating agent in the presence or absence of a solvent.

Examples of the dehydrating agent are polyphosphoric acid and concentrated sulfuric acid. The reaction solvent includes, for example, aromatic hydrocarbons such as toluene and xylene and halogenated hydrocarbons such as 1,2-dichloroethane, dichloromethane and chloroform. The reaction is completed in 5 minutes to 20 hours at 50° to 150° C.

Step 2

Compound (Ia) may be obtained by reacting Compound (III) with Compound (VI) in the presence of an acid catalyst in the presence or absence of a solvent.

Examples of the acid catalyst are inorganic acids such as hydrochloric acid, sulfuric acid and phosphoric acid, and organic acids such as acetic acid, p-toluenesulfonic acid and methanesulfonic acid. Examples of the solvent include aromatic hydrocarbons such as toluene and xylene, and alcohols such as methanol, ethanol and isopropanol. The reaction is completed in 5 minutes to 20 hours at 20° to 120° C.

Process 2

Compound (Ia) may be obtained from Compound (III) in accordance with the following reaction steps.

Step 1

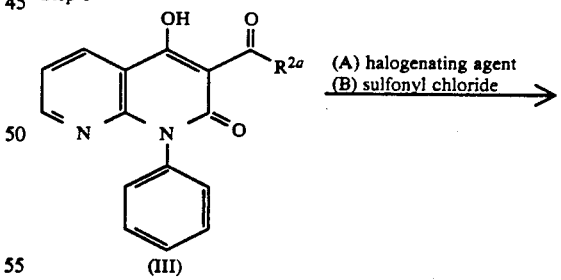

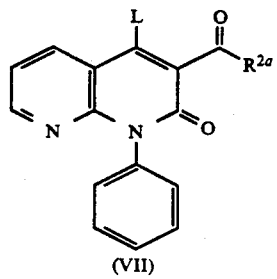

Step 2

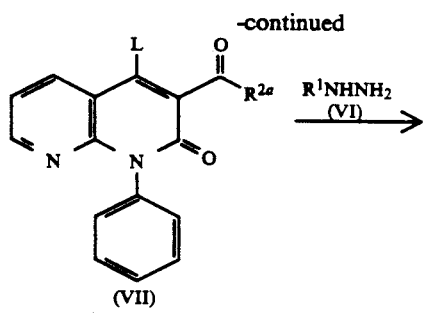

(VII)

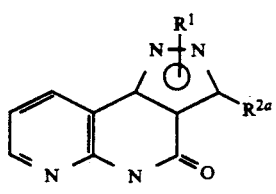

wherein $R^1$ and $R^{2a}$ are the same as defined above, L means a leaving group, and examples of the leaving group represented by L are halogen such as chlorine, bromine and iodine, or alkyl-substituted or aryl-substituted sulfonyloxy such as methanesulfonyloxy and p-toluenesulfonyloxy.

Step 1

[A]: Compound (VIIa) which is Compound (VII) wherein L is halogen is obtained by reacting Compound (III) with a halogenating agent in the presence or absence of a solvent, if required in the presence of a base.

Examples of the base include alkali metal carbonates such as potassium carbonate and sodium carbonate, alkali metal hydrides such as sodium hydride, alkali metal alkoxides such as sodium methoxide and sodium ethoxide, and alkylamines such as triethylamine. Any solvent can be used so long as it is inert to the reaction, and mention may be made of ethers such as tetrahydrofuran and dioxane, amides such as dimethylformamide, alcohols such as methanol and ethanol, hydrocarbons such as xylene, toluene, n-hexane and cyclohexane, halogenated hydrocarbons such as chloroform and carbon tetrachloride, and dimethylsulfoxide. These solvents are used alone or in combination. Examples of the halogenating agent include thionyl chloride, phosphorous oxychloride, phosphorous pentachloride, and phosphorous tribromide. The reaction is completed in 5 minutes to 24 hours at 0° to 150° C.

[B]: Compound (VIIb) which is Compound (VII) in which L is sulfonyloxy, may be obtained by reacting Compound (III) with sulfonyl chloride in the presence or absence of a base and a solvent.

The sulfonyl chloride includes, for example, alkyl- or aryl-substituted chlorides such as methanesulfonyl chloride and p-toluenesulfonyl chloride. The same base and solvent as mentioned in Process 2, Step 1 [A] can be used. The reaction is completed in 5 minutes to 24 hours at 0° to 100° C.

Step 2

Compound (Ia) may be obtained by reacting Compound (VII) with Compound (VI), if required in the presence of an acid catalyst. The same acid catalyst and the reaction solvent as mentioned in Process 1, Step 2 can be used. The reaction is completed in 5 minutes to 20 hours at 20° to 160° C.

Process 3

Compound (Iaa), which is Compound (I) wherein $R^1$ and $R^{2b}$ are the same as defined above, may be obtained in accordance with the following reaction steps.

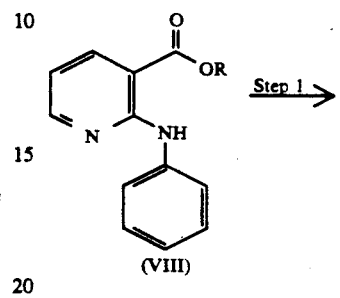

(VIII)

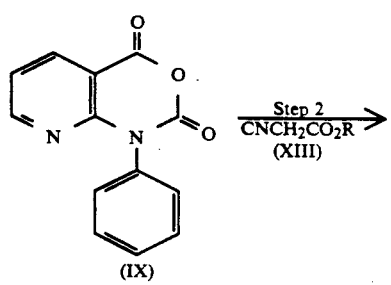

(IX)

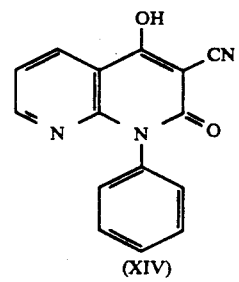

(XIV)

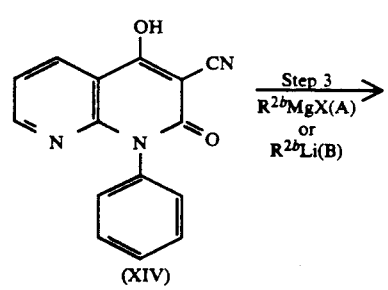

(XIV)

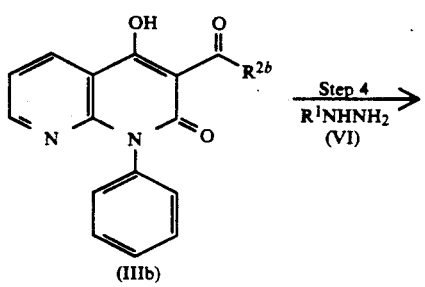

(IIIb)

-continued

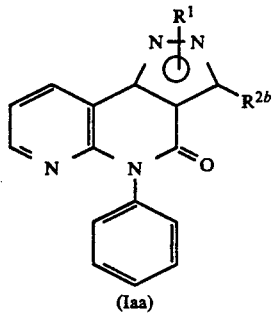

wherein $R^1$ and $R^{2b}$ are the same as defined above, R represents lower alkyl and X represents halogen.

The lower alkyl represents alkyl having 1-6 carbon atoms, and the halogen represents chlorine, bromine and iodine.

Step 1

Compound (IX) can be obtained by reacting Compound (VIII) with phosgene or trichloromethyl chloroformate (TCF), if required in a reaction solvent.

The starting Compound (VIII) can be synthesized by a known method as described in Journal of Organic Chemistry, 39, 1803, (1974) or according to the method.

The reaction solvent for use in the process is inert to the reaction and includes, for example, ethers such as tetrahydrofuran and dioxane, hydrocarbons such as toluene and n-hexane, and halogenated hydrocarbons such as 1,2-dichloroethane and chloroform. These solvents are used alone or in combination. The reaction is completed in 2 minutes to 24 hours at 0° to 200° C.

Step 2

Compound (XIV) is obtained by reacting Compound (IX) with Compound (XIII) in the presence or absence of a base.

The base used includes, for example, alkali metal carbonates such as potassium carbonate and sodium carbonate, alkali metal hydrides such as sodium hydride, and alkylamines such as triethylamine. The reaction solvent for use in the process is inert to the reaction and includes, for example, ethers such as tetrahydrofuran and dioxane, amides such as dimethylformamide, hydrocarbons such as xylene, toluene, n-hexane and cyclohexane, halogenated hydrocarbons such as chloroform and carbon tetrachloride, and dimethyl sulfoxide. These solvents are used alone or in combination. The reaction is completed in 5 minutes to 20 hours at 0° to 160° C.

Step 3

Compound (IIIb) may be obtained by reacting Compound (XIV) with an alkylating agent [(A) or (B)] and treating the reaction product with an acid. The acid includes, for example, hydrochloric acid, acetic acid and sulfuric acid.

The reaction solvent includes, for example, dioxane, tetrahydrofuran and diethyl ether and aromatic hydrocarbons such as toluene and xylene. The reaction is completed in 5 minutes to 20 hours at −30° to 100° C.

Step 4

Compound (Iaa) may be obtained by reacting Compound (IIIb) with Compound (VI) in the same method as described in Process 1, Step 2.

Process 4

Compound (Ib) which is Compound (I) wherein $R^1$ is the same as defined above and $R^2$ is hydroxy, may be obtained by the following steps.

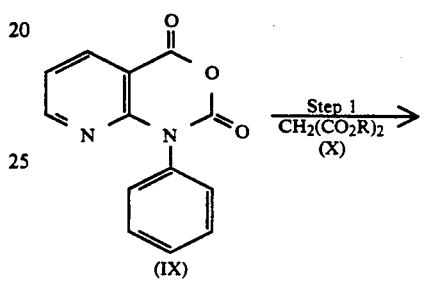

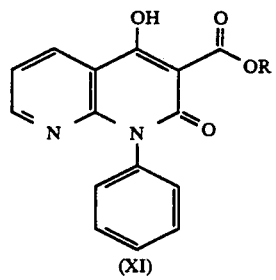

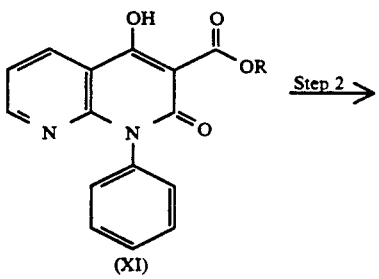

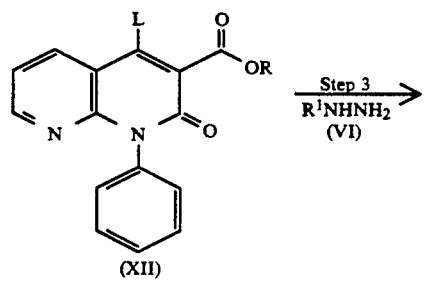

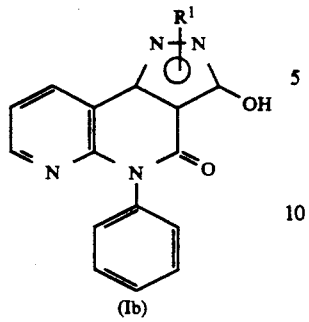

(Ib)

wherein R, L and R¹ are the same as defined above.

Step 1

Compound (XI) may be obtained by reacting Compound (IX) with Compound (X) in the presence or absence of a base.

The base used includes, for example, alkali metal carbonates such as potassium carbonate and sodium carbonate, alkyl metal hydrides such as sodium hydride, and alkylamine such as triethylamine. The reaction solvent for use in the process is inert to the reaction and includes, for example, ethers such as tetrahydrofuran and dioxane, amides such as dimethylformamide, hydrocarbons such as xylene, toluene, n-hexane and cyclohexane, halogenated hydrocarbons such as chloroform and carbon tetrachloride, and dimethyl sulfoxide. These solvents are used alone or in combination. The reaction is completed in 5 minutes to 24 hours at 0° to 200° C.

Step 2

Compound (XII) may be obtained from Compound (XI) according to a method similar to Process 2, Step 1.

Step 3

Compound (Ib) may be obtained by reacting Compound (XII) with Compound (VI).

The reaction solvent includes, for example, aromatic hydrocarbons such as toluene and xylene, and alcohols such as methanol, ethanol and isopropanol. The reaction is completed in 5 minutes to 24 hours at 0° to 120° C.

Process 5

Compound (Ic) which is Compound (I) wherein R¹ is the same as defined above, and R² is amino, may be obtained by the reaction steps shown below.

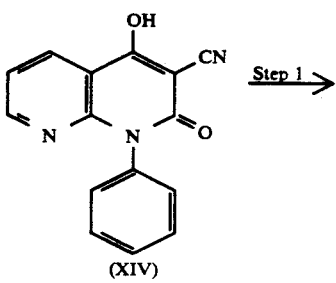

(XIV)

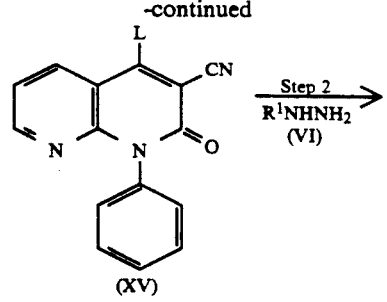

(XV)

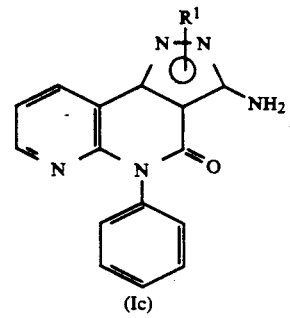

(Ic)

wherein L and R¹ are the same as defined above.

Step 1

Compound (XV) may be obtained from Compound (XIV) by the same method as described in Process 2, Step 1.

Step 2

Compound (Ic) may be obtained by reacting Compound (XV) with Compound (VI) in the same method as described in Process 4, Step 3.

Process 6

Compound (Iaaa) which is Compound (I) wherein R¹ is the same as defined above, and R² is a hydroxyl-substituted aryl, can be obtained by reacting Compound (Iaab) wherein R² is a methoxy-substituted aryl with a Lewis acid.

The Lewis acid includes, for example, aluminum chloride, aluminum bromide, boron trichloride, boron tribromide and boron triiodide. The reaction solvent includes, for example, aromatic hydrocarbons such as benzene, toluene and xylene, and halogenated hydrocarbons such as 1,2-dichloroethane and dichloromethane. The reaction is completed in 2 minutes to 20 hours at −80° to 150° C.

The intermediates and the final compounds in the above process can be isolated and purified by methods for purification conventionally used in organic synthetic chemistry, for example, filtration, extraction, washing, drying, concentration, recrystallization and various chromatographies. The intermediates may be served for the next reaction without any particular purification.

Where it is desired to obtain the salts of Compound (I), the salts may be purified as they are when the product is obtained in a salt form. Where the product is obtained in a free form, the product is dissolved or suspended in an appropriate solvent and an acid or a base is added to the solution or suspension to form its salt.

Compound (I) or its pharmaceutically acceptable salt may be present in the form of adducts with water or various solvents. These adducts are also included in the present invention.

Specific examples of Compound (I) obtained by the above various methods are shown in Table 1.

TABLE 1

| Compound No | −R$^1$ | −R$^2$ |
|---|---|---|
| 1 | −H | 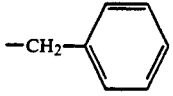 |
| 2 | −H | −CH$_3$ |
| 3 | −H | −CH$_2$CH(CH$_3$)$_2$ |
| 4 | −CH$_3$ | −CH$_3$ |
| 5 | −CH$_2$−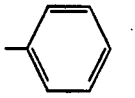 | −CH$_3$ |
| 6 | −CH$_3$ | −NH$_2$ |
| 7 | 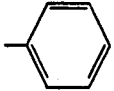 | −NH$_2$ |
| 8 |  | −OH |
| 9 | −H | −OH |
| 10 | −H |  |
| 11 | −H | −OCH$_3$ |
| 12 | −H | −N(CH$_3$)$_2$ |
| 13 | −H | 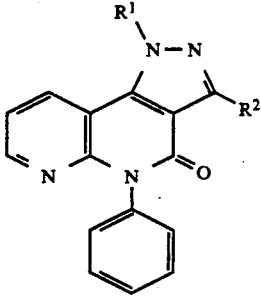−F |

TABLE 1-continued

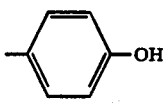

| Compound No | −R$^1$ | −R$^2$ |
|---|---|---|
| 14 | −H | (4-hydroxyphenyl)−OH |

The pharmacological tests of Compound (I) are described below.

(1) Plaque Forming Cell Assay

The plaque forming cell assay was performed by the following manner with reference to the method of Jerne [Science, 140, 405, (1963)] and the method of Yamamoto et al. [Drugs Exptl. Clin. Res., 8, 5, (1982)].

Male Balb/c stain mice (aged 7 weeks, SLC) were sensitized with $1 \times 10^8$ sheep red blood cells (Bio Test Research Institute), and 6 or 7 days after the sensitization, the spleen was extirpated. The cells obtained from the spleen were treated with ACT solution (tris-ammonium chloride isotonic buffer) to remove red blood cells. The cells were washed three times with an RPMI-1640 medium (Nissui Pharmaceutical Co., Ltd.). The spleen cells ($1 \times 10^7$ cells), the test compound dissolved in dimethyl sulfoxide and sheep blood red cells ($5 \times 10^6$) were suspended in an RPMI-1640 medium containing 10% bovine serum (Gibco Company), 2-mercaptoethanol ($5 \times 10^{-5}$M), 50 µg/ml of streptomycin and 50 IU/ml of penicillin. The suspension was distributed into a microculture plate (NUNC Co., Ltd., 24 holes), and incubated for 5 days in a carbon dioxide gas incubater at 37° C.

After the termination of incubation, the cells were transferred to a plastic test tube. The supernatant was removed by centrifugal separation (2000 rpm), and the pellet was re-suspended in 1 ml of an RPMI-1640 culture medium. The cell suspension, sheep blood red cells, and guinea pig complement (Cedarlene Institute) were incubated by the method of Cunningham [Immunology, 14, 599, (1968)], at 37° C. for 1 to 2 hours. The appearing direct plaque cells (PFC count) in suspension were counted. From the resulting PFC count, the inhibition rate of the antibody production of the test compound was determined by the following formula.

$$\text{Inhibition rate (\%)} = \frac{A - B}{A} \times 100$$

A: PFC count in the absence of test compound (dimethylsulfoxide alone)
B: PFC count in the presence of test compound
The results are shown in Table 2.

TABLE 2

| Compound No. | Inhibition rate (%) | |
|---|---|---|
| | $10^{-6}$M | $10^{-5}$M |
| 1 | 77.2 | 85.8 |
| 2 | 85.8 | 92.4 |
| 3 | 77.2 | 74.9 |
| 4 | — | 81.4 |
| 6 | — | 76.5 |
| 7 | — | 83.8 |
| 10 | 57.1 | 83.9 |
| 11 | 26.5 | 99.5 |

Depression of function of T cells produce hypertension of B cells, and autoimmune diseases such as rheumatoid arthritis are considered to be a tissue injury which is caused by hypertension of B cells. Therefore, Compound (I), which inhibits antibody production, is expected to have effect on autoimmune diseases.

(2) Passive Schultz-Dale (S-D) Reaction

Male Hartley guinea pigs weighing 350 to 500 g were passively sensitized by intraperitoneal injection of rabbit anti-OA serum prepared in advance by the method of Koda et al. [Folia Pharmacol., Japon 66, 237, (1970)]. After 24 hours, the guinea pigs were stunned and exsanguinated, and then tracheae were removed. The zig-zag strips of the tracheae were prepared by the method of Emmerson and Mackay [J. Pharm. Pharmacol., 31, 798, (1979)]. The strips were suspended in Krebs-Henseleit solution at 37° C. under aeration of a mixed gas of 95% oxygen and 5% carbon dioxide, and equilibrated for one hour. Then, antigen (egg white albumin) was introduced in the solution (final concentration; 1 μg/ml), and the contraction was measured by isotonictransducer (TD-112s, Nihon Kohden Co., Ltd.) and recorded on a recorder (Type 3066, Yokogawa-Hokushin Denki, Co., Ltd.). After the contraction curves reached a plateau, the test compounds were successively added in order to get cumulative concentration-relaxation curves. The concentration of 50% relaxation rate ($IC_{50}$) was culculated from the regression line, which was obtained from the cumulative concentration-relaxation curves.

The results are shown in Table 3.

(3) Inhibition Effect on Platelet Activating Factor (PAF)-Induced Mortality

The experiment was performed by a minor modification of method of Carlson et al. [Agents and Actions, 21, 379 (1987)]. Groups each consisting of 10 male dd mice (weighing 28 to 32 g) were used, and 100 mg/kg of test compound or a saline (control) was orally administered. One hour after the administration of test compound, 40 μg/kg of PAF (manufactured by Avanti Polar Lipids Co., Ltd.) was intravenously administered. Two hours after PAF injection, the mortality rate of the animals was observed. The compound whose mortality rate was significantly (p<0.05: Fischer's accurate probability tests) lower than control is regarded as having inhibitory effect on PAF-induced mortality, and the results in Table 3 were represented by minimum effective dose (MED).

TABLE 3

| Compound No. | Passive S-D reaction $IC_{50}$ (μM) | Inhibition of PAF-induced mortality MED (mg/kg) |
|---|---|---|
| 1 | 3.15 | 10 |
| 3 | 0.258 | 5 |
| 10 | 0.708 | — |

(4) Hair Growth Stimulation

Effect of test compound on hair growth in mice was examined. Hair on the back of male C3H/HeSlc-strain mice aged 9 weeks, which was in the telogen of hair cycle was clipped off by an electric hair-clipper. The test compound dissolved in a solvent mixture [ethanol:-propyleneglycol (6:4)] was uniformly applied to the hair removed area of the mice once a day. Concentration of the test compound was shown in Table 4. The group which received the solvent mixture alone was used as control.

TABLE 4

| Compound | Concentration of Compound (%) |
|---|---|
| 1 | 0.14 |
| 3 | 1.00 |

Hair growth stimulation was estimated by measuring the ratio of the hair growing area to the test compound treated area by photograph. In the test compound received group, darkening of intraderma (indicating the formation of hair follicles) was observed on the 10th day, and then hair growth rapidly progressed. On the 16th day, marked hair growth was observed in most of the test compound treated area. In contrast, on the 16th day of the control group, darkening of intraderma was observed only in the part of the solvent treated area and hair growth scarcely occurred Table 5 shows the ratio of hair growing area to the test compound treated area on the 16th day.

TABLE 5

| Compound | Hair growing area (%) Mean ± S.D. |
|---|---|
| Control | 10.2 ± 3.4 |
| 1 | 91.5 ± 8.0 |
| 3 | 91.8 ± 7.2 |

Furthermore, in the test compound received group, a complete regeneration of hair was observed on about 20th day. During experiment, on the test compound treated area of skin, abnormality such as dermatitis was not observed.

(5) Acute Toxicity Test

Male dd-stain mice weighing 20–25 g, groups each consisting of 3 animals, were used, and Compound 1 and Compound 3 were orally administered. MLD was determined by observing the mortality for seven days after the administration. MLD of both compounds were over 300 mg/kg.

These results of pharmacological tests 1–4 suggest that Compound (I) is expected to have immuno-suppressive effect, broncho-dilatory effect, antiinflammatory effect and hair growth-stimulative effect.

Compound (I) or its pharmaceutically acceptable salt may be used singly as they are, but it is generally preferred that these compounds be administered or in the form of various pharmaceutical preparations. The pharmaceutical composition of this invention is produced by uniformly mixing, as an active ingredient, an effective amount of Compound (I) or its pharmaceutically acceptable salt with a pharmaceutically acceptable carrier. These pharmaceutical compositions are desirably in dosage forms for oral administration, administration by injection, percutaneous administration or administration by inhalation.

In the preparation of compositions for oral dosage forms such as liquid preparation, powders, pills, capsules, and tablets, any of useful pharmaceutically acceptable carriers are used. In the case of orally administered liquid preparations such as suspensions and syrups may be prepared by using water, sugars such as sucrose, sorbitol or fructose, glycols such as polyethylene glycol or propylene glycol, oils such as sesame oil, olive oil and soybean oil, antiseptics such as p-hydroxybenzoic acid esters, and flavors such as strawberry flavor, and peppermint flavor. In the case of powders, pills, capsules and tablets, they may be produced by using vehicles such as lactose, glucose, sucrose, and mannitol, disintegrators such as starch and sodium alginate, lubricants such as magnesium stearate and talc, binders such as polyvinyl alcohol, hydroxypropyl cellulose and gelatin, surfactants such as fatty esters, and plasticizers such as glycerol.

A liquid preparation suitable for injection is prepared by using a carrier such as water, distilled water, a salt solution, a glucose solution and a mixture of a salt water and a glucose solution.

Dosage form in case of precutaneous administration is dosage forms for external use, for example, lotion, liniment, emulsion and spray.

In the preparation of compositions suitable for dosage forms for external use, any of useful pharmaceutically acceptable carriers and annexes are used. As the pharmaceutically acceptable carriers and annexes, mention may be made of antibacterial drugs such as phenol and benzalkonium chloride, refrigrants such as menthol, ester-type oils such as isopropyl myristate and 2-ethylhexylparmitate, polyhydric alcohols such as glycerol and sorbitol, wetting agents such as mucopolysaccharide, lower alcohols such as ethanol, water, vitamins, hormones, amino acids, surfactants, solubilizers, antioxidants, ultraviolet-absorbing agents, perfumery and pigments. These carriers and annexes are used alone or in combination.

An aerosol for inhalation administration may be prepared by dissolving Compound (I) in a suitable pharmaceutically acceptable solvent, such as ethyl alcohol or a mixture of ethyl alcohol and miscible solvent and mixing the solution with a pharmaceutically acceptable propellant.

The effective dose and the number of administrations of Compound (I) or its pharmaceutically acceptable salt may differ depending upon the form of administration, the age, the body weight and the condition of the patient. In oral administration, it is preferable to usually administer 1 to 50 mg/kg of Compound (I) or its pharmaceutically acceptable salt daily in 3 to 4 portions.

In precutaneous administration, it is preferable to usually apply 0.0001-500 mg of Compound (I) or its pharmaceutically acceptable salt once a day or by dividing the application amount into 2 to 4 portions.

The embodiments of this invention will be illustrated by Examples, Reference Examples and Preparation Examples.

EXAMPLES

Example 1

3,5-Diphenyl-1H-pyrazolo[4,3-c][1,8]naphthyridin-4(5H)-one (Compound 1)

Benzoyl chloride, 1.75 ml (15.1 millimoles), was added to nitrobenzene (30 ml) containing 5.0 g (37.8 millimoles) of aluminum chloride under an argon atmosphere, and the mixture was stirred for 1 hour at room temperature to form a uniform solution. To the solution was added 3.0 g (12.6 millimoles) of 4-hydroxy-1-phenyl[1,8]naphthyridin-2(1H)-one, and the mixture was stirred at 160° to 170° C. for 6 hours. Dilute hydrochloric acid was added to the reaction mixture, and the mixture was extracted with chloroform. The extract was dried over anhydrous magnesium sulfate. The solvent was evaporated under reduced pressure, and the crude product was recrystallized from dimethylformamide (DMF)-water to obtain 2.6 g (yield 59.6%) of 3-benzoyl-4-hydroxy-1-phenyl[1,8]naphthyridin-2-(1H)-one (Compound 101).

850 mg (2.5 millimoles) of Compound 101 was suspended in 5 ml of glacial acetic acid, and 0.26 ml (5.5 millimoles) of hydrazine monohydrate was added to the suspension. The mixture was heated under reflux for 5 hours and the reaction mixture was cooled to room temperature. The precipitate was collected by filtration, and recrystallized from DMF-water to obtain 440 mg (yield 52.4%) of Compound 1.

Melting point: >300° C.

Elemental analysis (%): for $C_{21}H_{14}N_4O.0.6H_2O$. Calculated: C72.36, H4.39, N 16.05. Found: C 72.36, H 4.06, N 15.74.

IR (KBr) cm$^{-1}$: 3550–3350(br), 1640, 1600, 1580

NMR ($CF_3CO_2D$) δ(ppm): 9.47 (1H, dd, J=8.4, 1.3), 8.52 (1H, dd, J=6.2, 1.2), 8.07–7.37 (11H, m)

MS (m/e): 338, 337, 280

Example 2

3-Methyl-5-phenyl-1H-pyrazolo[4,3-c][1,8]naphthyridin-4(5H)-one (Compound 2)

4-Hydroxy-1-phenyl[1,8]naphthyridin-2(1H)-one, 20.0 g (84.0 millimoles), was added to 170 ml of glacial acetic acid and 340 ml of polyphosphoric acid. The mixture was stirred at 100° to 110° C. for 5 hours. The reaction solution was poured into water and the mixture was stirred for 1 hour. The precipitate was collected by filtration, and recrystallized from DMF-water to give 18.3 g (yield: 77.6%) of 3-acetyl-4-hydroxy-1phenyl[1,8]naphthyridin-2(1H)-one (Compound 102).

Compound 102 in an amount of 1.2 g (4.3 millimoles) was suspended in 10 ml of glacial acetic acid, and 0.46 ml (9.4 millimoles) of hydrazine monohydrate was added to the suspension. Thereafter, the mixture was heated under reflux for 3 hours. The reaction solution was cooled to room temperature, and the precipitate was collected by filtration and recrystallized from DMF-water to give 530 mg (yield: 44.3%) of Compound 2.

Melting point: >300° C.

Elemental analysis (%): for $C_{16}H_{17}N_4O.0.9H_2O$. Calculated: C 65.69, H 4.61, N 18.89. Found: C 65.70, H 4.76, N 19.15.

IR (KBr) cm$^{-1}$: 3600–3000 (br), 1660, 1600, 1590

NMR (CF$_3$CO$_2$D) δ(ppm): 9.36 (1H, dd, J=7.5, 1.3), 8.48 (1H, dd, J=6.0, 1.2), 8.05–7.65 (4H, m), 7.60–7.35 (2H, m), 2.95 (3H, s)

MS (m/e): 276, 275

Example 3

3-Isobutyl-5-phenyl-1H-pyrazolo[4,3-c][1,8]naphthyridin-4(5H)-one (Compound 3)

Isovaleric acid (2 ml) and 5 ml of polyphosphoric acid were added to 200 mg (0.84 millimole) of 4-hydroxy-1-phenyl[1,8]naphthyridin-2(1H)-one, and the mixture was stirred at 130° C. for 6 hours. The reaction solution was poured into water, and the mixture was further stirred for one hour. The reaction solution was extracted with chloroform, and the solvent was evaporated under reduced pressure. Water-methanol was added to the residue and the precipitate was collected by filtration. The precipitate was recrystallized from DMF-water to give 170 mg (yield: 62.9%) of 3-isobutyl-4-hydroxy-1-phenyl[1,8]naphthyridin-2(1H)-one (Compound 103).

Compound 103, 150 mg (0.47 millimole) was suspended in 2 ml of glacial acetic acid, 0.05 ml (1.02 millimole) of hyrazinemonohydrate was added to the suspension. The mixture was heated under reflux for 1.5 hours. The reaction solution was cooled to room temperature, and the precipitate was collected by filtration and recrystallized from DMF-water to give 40 mg (yield 27.0%) of Compound 3.

Melting point: 217°–220° C.

Elemental analysis (%): for C$_{19}$H$_{18}$N$_4$O. Calculated: C 71.68, H 5.70, N 17.60. Found: C 72.07, H 5.73, N 16.77.

IR (KBr) cm$^{-1}$: 3620–3200 (br), 1690, 1660, 1610, 1590.

NMR (CF$_3$CO$_2$D) δ(ppm): 9.34 (1H, dd, J=7.8, 1.6), 8.49 (1H, dd, J=8.1, 1.2), 7.90–7.37 (7H, m), 3.20 (2H, d, J=7.2), 2.53–1.90 (1H, br), 1.05 (6H, d, J=6.1).

MS (m/e): 318, 317, 303, 275.

Example 4

1,3-Dimethyl-5-phenyl-1H-pyrazolo[4,3-c][1,8]naphthyridin-4(5H)-one (Compound 4)

Compound 102 obtained in Example 2, 4.0 g (14.3 millimoles), was suspended in 2.5 ml of glacial acetic acid, and 1.8 ml (34.2 millimoles) of methylhydrazine was added to the suspension. The mixture was heated under reflux for 10 hours. The reaction solution was cooled to room temperature, and the precipitate was collected by filtration and recrystallized from DMF-water to give 2.5 g (yield: 60.1%) of Compound 4.

Melting point: >300° C.

Elemental analysis (%): for C$_{17}$H$_{14}$N$_4$O. Calculated: C 70.33, H 4.86, N 19.30. Found: C 70.20, H 4.73, N 18.83.

IR (KBr) cm$^{-1}$: 3620–3110 (br), 1660, 1610, 1580, 1495, 1400.

NMR (CF$_3$CO$_2$D) δ(ppm): 9.41 (1H, dd, J=7.8, 1.2), 8.54 (1H, dd, J=6.5, 1.3), 8.07–7.67 (4H, m), 7.64–7.34 (2H, m), 4.63 (3H, s), 2.82 (3H, s).

MS (m/e): 290, 289, 275

Example 5

1-Benzyl-3-methyl-5-phenyl-1H-pyrazolo[4,3-c][1,8]naphthyridin-4(5H)-one (Compound 5)

Compound 102 obtained in Example 2, 3.0 g (10.7 millimoles), was suspended in 20 ml of glacial- acetic acid, and 3.1 g (16.1 millimoles) of benzylhydrazine dihydrochloride and 9.0 ml (64.2 millimoles) of triethylamine were added to the suspension. The mixture was heated under reflux for 10 hours. The reaction solution was cooled to room temperature, and the precipitate was collected by filtration and recrystallized from DMF-water to give 2.4 g (61.5%) of Compound 5.

Melting point: 274°–276° C.

Elemental analysis (%): for C$_{23}$H$_{18}$N$_4$O. Calculated: C 75.39, H 4.95, N 15.29 Found C 75.34, H 4.82, N 15.29.

IR (KBr) cm$^{-1}$: 3600–3300 (br), 1660, 1570, 1490, 1400.

NMR (CF$_3$CO$_2$D) δ(ppm): 8.97 (1H, dd, J=7.8, 1.2), 8.43 (1H, dd, J=6.9, 1.2), 7.90–7.08 (11H, m), 6.18 (1H, s), 2.90 (3H, s).

MS (m/e): 366, 365, 275.

Example 6

3-Amino-1-methyl-5-phenyl-1H-pyrazolo[4,3-c][1,8]naphthyridin-4(5H)-one (Compound 6)

134 ml (1.44 moles) of phosphorus oxychloride was added to 27 g (0.10 mole) of Compound c obtained in Reference Example 3 under ice cooling. The mixture was heated under reflux for 4 hours. The solution was cooled to room temperature, and the excess of phosphorus oxychloride was evaporated under reduced pressure. With ice cooling, water was added to the resulting residue, and the mixture was neutralized with 8N sodium hydroxide aqueous solution. The resulting crystals were collected by filtration and dried to give 27 g of crystals. Out of them, 2 g of the crystals was suspended in 100 ml of ethanol, and 0.76 ml (0.014 mole) of methylhydrazine was added to the suspension. The mixture was heated under reflux for 2 hours. The solution was cooled, and the resulting crystals were collected by filtration and recrystallized from DMF to obtain 1.6 g (yield: 73%) of Compound 6.

Melting point: >300° C.

Elemental Analysis (%): for C$_{16}$H$_{13}$N$_5$O. Calculated: C 65.96, H 4.49, N 24.04 Found: C 65.91, H 4.29, N 24.10.

IR (KBr) cm$^{-1}$: 3750, 3690, 3650, 1662.

MS (m/e): 291 (M+), 290.

Example 7

3-Amino-2,5-diphenyl-2H-pyrazolo[4,3-c][1,8]naphthyridin-4(5H)-one (Compound 7)

Except that phenylhydrazine was used instead of methylhydrazine, the same procedure as described in Example 6 was repeated to obtain Compound 7 in a yield of 86%.

Elemental Analysis (%): for C$_{21}$H$_{15}$N$_5$O. Calculated: C 71.37, H 4.27, N 19.81. Found: C 71.44, H 4.29, N 20.11.

MS (m/e): 353 (M+), 352.

Example 8

3-Hydroxy-2,5-diphenyl-2H-pyrazolo[4,3-c][1,8]naphthyridin-4(5H)-one (Compound 8)

Except that Compound b obtained in Reference Example 2 was used instead of Compound c obtained in Reference Example 3, the same procedure as described in Example 7 was repeated to give Compound 8 in a yield of 26%.

Elemental Analysis (%): for $C_{21}H_{14}H_4O_2$. Calculated: C 71.17, H 3.98, N 15.81. Found: C 70.67, H 3.92, N 15.49.

MS (m/e): 354 (M+), 319, 275, 261.

Example 9

3-Hydroxy-1H-pyrazolo[4,3-c][1,8]naphthyridin-(5H)-one (Compound 9)

Except that hydrazine hydrate was used instead of phenylhydrazine, the procedure of Example 7 was repeated to give Compound 9 in a yield of 22%.

Melting point: >300° C..

Elemental Analysis (%): for $C_{15}H_{10}N_4O_2.H_2O$. Calculated: C 60.80, H 4.08, N 18.91. Found: C 60.93, H 3.98, N 18.96.

IR (Kbr) cm.: 1661, 1644.

MS (m/e): 278 (M+), 277.

Example 10

5-Phenyl-3-thienyl-1H-pyrazolo[4,3-c][1,8]naphthyridin-4(5H)-one (Compound 10)

In an argon atmosphere, 5.0 g (19.0 millimoles) of the Compound c obtained in Reference Example 3 was suspended in 100 ml of tetrahydrofuran. 2-Thienyl magnesium bromide (60.8 millimoles) in tetrahydrofuran was added to the suspension under ice cooling. The mixture was stirred at 60° C. for one hour, and dilute hydrochloric acid was added to the reaction mixture. The mixture was heated under reflux for 5 hours. The reaction solution was cooled to room temperature. Then, the precipitate was collected by filtration, and recrystallized from DMF-water to give 5.1 g (yield: 77.1%) of 4-hydroxy-1-phenyl-3-thenoyl[1,8]naphthyridin-2-(1H)-one (Compound 104).

Compound 104, 2.0 g (5.7 millimoles), was suspended in 60 ml of glacial acetic acid, and 0.42 ml (8.6 millimoles) of hydrazine monohydrate was added to the suspension. The mixture was heated under reflux for 6 hours. The reaction mixture was cooled to room temperature and the precipitate was collected by filtration. Recrystallization from DMF-water gave 1.2 g (yield: 61.3%) of Compound 10.

Melting point: >300° C.

Elemental analysis (%): for $C_{19}H_{12}N_4OS.0.3H_2O.0.6DMF$. Calculated: C 63.46, H 4.30, N 16.37. Found: C 63.37, H 4.24, N 16.43.

IR (KBr) cm$^{-1}$: 1649, 1577

NMR (DMSO-d$_6$) δ(ppm): 8.57 (1H, dd, J=7.1, 1.6), 8.47–8.42 (2H, m), 7.95 (1H, s), 7.57–7.29 (7H, m), 7.11 (1H, t, J=4.3)

MS (m/e): 344, 343, 314, 286

Example 11

3-(4-methoxyphenyl)-5-phenyl-1H-pyrazolo[4,3-c][1,8]naphthyridin-4(5H)-one (Compound 11)

In an argon atmosphere, 4.0 g (15.2 millimoles) of Compound c obtained in Reference Example 3, was suspended in 80 ml of tetrahydrofuran. 4-Methoxyphenyl magnesium bromide (33.4 millimoles) in tetrahydrofuran was added to the suspension under ice cooling. The mixture was stirred at room temperature for 1.5 hours, diluted hydrochloric acid was added to the reaction mixture, and the solution was heated under reflux for 2 hours. The reaction solution was cooled to room temperature, and the precipitate was collected by filtration, and recrystallized from DMF-water to give 4.7 g (yield 83.3%) of 4-hydroxy-3-(4-methoxy)phenyl-1-phenyl[1,8]naphthyridin-2(1H)-one (Compound 105).

Compound 105, 2.5 g (6.7 millimoles), was suspended in 60 ml of glacial acetic acid and 0.81 ml (16.8 millimoles) of hydrazine monohydrate was added to the suspension. The mixture was heated under reflux for 2.5 hours. The reaction mixture was cooled to room temperature, and the precipitate was collected by filtration and recrystallized from DMF-water to obtain 1.0 g (yield: 41.3%) of Compound 11.

Melting point: >300° C.

Elemental analysis (%): for $C_{22}H_{16}N_4O_2.0.5DMF$. Calculated: C 69.70, H 4.85, N 15.56. Found: C 69.66, H 5.01, N 15.48.

IR (KBr) cm$^{-1}$: 1651, 1518

NMR (DMSO-d$_6$) δ(ppm): 8.57 (1H, dd, J=7.8, 1.7), 8.38 (1H, dd, J=4.8, 1.7), 8.14 (2H, d, J=8.9), 7.95 (1H, s), 7.55–7.42 (3H, m), 7.41–7.27 (3H, m), 7.02 (2H, d, J=8.9), 3.81 (3H, s).

MS (m/e): 368, 352, 324, 295

Example 12

3-(4-Dimethylaminophenyl)-5-phenyl-1H-pyrazolo[4,3-c][1, 8]naphthyridin-4(5H)-one (Compound 12)

In an argon atmosphere, 4.0 g (15.2 millimoles) of Compound c obtained in Reference Example 3 was suspended in 80 ml of tetrahydrofuran. 4-Dimethylaminophenylmagnesium bromide (33.4 millimoles) in tetrahydrofuran was added to the suspension under ice cooling. The mixture was stirred at room temperature for 1.5 hours, dilute hydrochloric acid was added to the reaction mixture, and the mixture was heated under reflux for 2 hours. The reaction mixture was cooled to room temperature. The precipitate was collected by filtration and recrystallized from DMF-water to give 4.0 g (yield 68.9%) of 3-(4-dimethylamino)phenyl-4-hydroxy-1-phenyl[1,8]naphthyridin-2-(1H)one (Compound 106).

Compound 106, 2.0 g (5.2 millimoles), was suspended in 50 ml of glacial acetic acid. After adding 0.63 ml (13.0 millimoles) of hydrazine monohydrate to the suspension, the mixture was heated under reflux for 1 hour. The reaction mixture was cooled to room temperature, and the precipitate was collected by filtration, and recrystallized from DMF-water to give 0.96 g (yield: 48.6%) of Compound 12.

Melting point: >300° C.

Elemental analysis (%): for $C_{23}H_{19}N_5O$. Calculated: C 72.42, H 5.02, N 18.36. Found: C 72.49, H 5.09, N 18.43.

IR (KBr) cm$^{-1}$: 1678, 1610

NMR (DMSO-d$_6$) δ(ppm): 8.55 (1H, dd, J=7.6, 1.6), 8.35 (1H, dd, J=4.6, 1.6), 8.06 (2H, d, J=8.9), 7.54–7.43 (3H, m), 7.34–7.26 (3H, m), 6.77 (2H, d, J=9.2), 2.96 (6H, s).

MS(m/e): 381, 380, 364

Example 13

5-Phenyl-3-(4-fluorophenyl)-1H-pyrazolo[4,3-c][1, 8]naphthyridin-4(5H)-one (Compound 13)

In an argon atmosphere, 3.5 g (13.3 millimoles) of Compound c obtained in Reference Example 3 was suspended in 70 ml of tetrahydrofuran. 4-Fluorophenylmagnesium bromide (29.3 millimoles) in tetrahydrofuran was added to the suspension under ice cooling. The mixture was stirred at room temperature for 2.5 hours, dilute hydrochloric acid was added to the mixture, and the solution was heated under reflux for 8 hours. The reaction mixture was cooled to room temperature, and the precipitate was collected by filtration, and recrystallized from DMF-water to obtain 3.8 g (yield: 80.7%) of 4-hydroxy-1-phenyl-3-(4fluorophenyl)[1,8]naphthyridin-2(1H)-one (Compound 107).

Compound 107, 2.5 g (6.9 millimoles), was suspended in 50 ml of glacial acetic acid. After adding 0.40 ml (8.3 millimoles) of hydrazine monohydrate to the suspension, the mixture was heated under reflux for 2 hours. The reaction mixture was cooled to room temperature, and the precipitate was collected by filtration and recrystallized from DMF-water to give 1.6 g (yield: 64.7%) of Compound 13.

Melting point: 300° C.
Elemental analysis (%): for $C_{21}H_{13}FN_4O.0.8DMF$. Calculated: C 67.75, H 4.52, N 16.21. Found: C 67.63, H 4.65, N 16.09.
IR (KBr) cm$^{-1}$: 1655, 1597, 1520
NMR (DMSO-d$_6$) δ(ppm): 8.59 (1H, d, J=6.9), 8.41–8.27 (3H, m), 7.55-7.27 (8H, m)
MS (m/e): 360, 359, 331, 265

Example 14

3-(4-Hydroxyphenyl)-5-phenyl-1H-pyrazolo[4,3-c][1,8]naphthyridin-4(5H)-one (Compound 14)

In an argon atmosphere, 2.3 g (6.2 millimoles) of Compound 11 obtained in Example 11 was dissolved in 100 ml of methylene chloride. The solution was cooled to 0° C. Slowly 1.8 ml (18.7 millimoles) of boron tribromide was added to the solution, and the mixture was stirred at room temperature for 7 hours. The reaction mixture was cooled to 0° C., and then 30 ml of methanol was added. The mixture was stirred at room temperature for 30 minutes. ¾ volume of the solvent was evaporated under reduced pressure. 18 ml of 3N hydrochloric acid was added. The precipitate was collected by filtration, and recrystallized from DMF-water to obtain 2.1 g (yield: 96.3%) of Compound 14.

Melting point: >300° C.
Elemental analysis (%): for $C_{21}H_{14}N_4O_2.0.4H_2O.0.4DMF$. Calculated: C 68.23, H 4.54, N 15.77. Found: C 68.13, H 4.71, N 15.73.
IR (KBr) cm$^{-1}$: 3220–3100 (br), 1660, 1640, 1610
NMR (DMSO-d$_6$) δ(ppm): 10.30–9.69 (1H, br), 8.57 (1H, dd, J=7.7, 1.5), 8.37 (1H, dd, J=4.7, 1.5), 8.03 (2H, d, J=8.4), 7.95–7.26 (6H, m), 6.84 (2H, d, J=8.9)
MS (m/e): 354, 353, 324, 296

Reference Example 1

1-Phenyl-2H-pyrido[2,3-d][1,3]oxazine-2,4m(1H)-dione (Compound a)

7.0 g (0.031 mole) of methyl 2-anilinonicotinate (J. Org. Chem., Vol. 39, page 1803, 1974) was dissolved in a mixture of 70 ml of 1,2-dichloroethane and 7 ml of dioxane. With stirring at 60° C., 11 ml (0.092 mole) of trichloromethyl chloroformate was added to the solution. The mixture was refluxed for 3 hours. After slight cooling, 0.25 g of activated charcoal was added to the reaction mixture, and the reaction mixture was further refluxed for 30 minutes in a stream of nitrogen. The mixture was cooled to room temperature, filtered and concentrated. The precipitated crystals were recrystallized from dichloromethane diisopropyl ether to give 6.5 g (yield: 87%) of Compound a as a colorless crystals.

Melting point: 196°–198° C.
Elemental analysis (%): for $C_{13}H_8N_2O_3$. Calculated: C 65.00, H 3.36, N 11.66. Found: C 65 11, H 3.22, N 11.48.
IR (KBr) cm$^{-1}$: 1791, 1727, 1584
NMR (DMSO-d$_6$) δ(ppm): 8.58 (1H, dd, J=5, 2Hz), 8.48 (1H, dd, J=8, 2Hz), 7.51–7.63 (3H, m), 7.33–7.37 (2H, m), 7.29 (1H, dd, J=8, 5Hz)
MS (m/e): 240(M+), 196, 168.

Reference Example 2

3-Ethoxycarbonyl-4-hydroxy-1-phenyl-1,8-naphthyridin-2(1H)-one (Compound b)

Diethyl malonate, 25 ml(0.016 mole), was dissolved in 25 ml of N,N-dimethylacetamide, and 0.80 g (0.020 mole) of 60% sodium hydride was added to the solution with cooling. After hydrogen ceased to be evolved, 1.0 g (0.017 mole) of Compound a obtained in Reference Example 1 was added. The mixture was gradually warmed, and heated at 150° C. for 2.5 hours. The reaction solution was cooled, 100 ml of ethyl acetate was added, and the precipitated crystals were collected by filtration. The resulting crystals were dissolved in 100 ml of water, the solution was acidified with concentrated hydrochloric acid, and the precipitated crystals were collected by filtration. The crystals were washed with water, dried under reduced pressure, and recrystallized with isopropyl alcohol-ethanol to obtain 4.3 g (yield: 88%) of Compound b as colorless crystals.

Reference Example 3

3-Cyano-4-hydroxy-1-phenyl-1,8-naphthyridin-2(1H)-one (Compound c)

1.6 ml (0.020 mole) of ethyl cyanoacetate was dissolved in 25 ml of N, N-dimethylacetamide, and 0.80 g (0.020 mole) of 60% sodium hydride was added with ice cooling. After hydrogen ceased to be evolved, 4.0 g (0.017 mole) of Compound a obtained in Reference Example 1 was added. The mixture was gradually warmed, and stirred at 100° C. for 30 minutes. The solution was cooled to room temperature, the solvent was evaporated under reduced pressure and water was added. The mixture was washed with ethyl acetate, the aqueous layer was acidified with concentrated hydrochloric acid, and the resulting crystals were collected by filtration. The crystals were recrystallized with ethanol to give 1.1 g (yield: 48%) of Compound c.

Melting point: >300° C.
Elemental analysis (%): for $C_{15}H_9N_3O_2$. Calculated: C 68.43, H 3.44, N 15.96. Found: C 68.43, H 3.12, N 15.85.
IR (KBr) cm$^{-1}$: 2234, 1552, 778.
NMR (CF$_3$CO$_2$D) δ(ppm): 8.44–8.42 (2H, m), 7.38–7.56 (3H, m), 7.21–7.35 (3H, m).
MS (m/e): 263 (M ), 262, 195, 77.

Preparation Example 1: (tablets)

By a conventional method, tablets of the following composition were prepared.

| | |
|---|---|
| Compound 1 | 20 mg |
| Lactose | 60 mg |
| Potato starch | 30 mg |
| Polyvinyl alcohol | 3 mg |
| Magnesium stearate | 1 mg |

Preparation Example 2: (powder)

By a conventional method, a powder of the following composition was prepared.

| Compound 1 | 20 mg |
|---|---|
| Lactose | 300 mg |

Preparation Example 3: (syrup)

By a conventional method, a syrup of the following composition was prepared.

| Compound 1 | 20 mg |
|---|---|
| Purified white sugar | 30 mg |
| Ethyl p-hydroxybenzoate | 40 mg |
| Propyl p-hydroxybenzoate | 10 mg |
| Strawberry flavor | 0.1 cc |

Water was added to the total volume amounts to be 100 cc.

Preparation Example 4: (capsules)

By a conventional method, capsules of the following composition were prepared.

| Compound 1 | 20 mg |
|---|---|
| Lactose | 200 mg |
| Magnesium stearate | 5 mg |

These compounds were mixed and filled in gelatin capsules.

What is claimed is:

1. A pyrazolonaphthyridine compound represented by the formula:

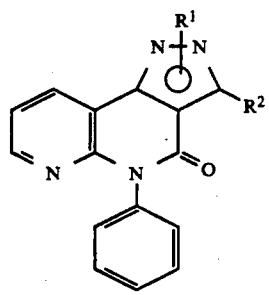

wherein $R^1$ represents hydrogen, lower alkyl, aralkyl, or substituted or unsubstituted aryl, $R^2$ represents hydrogen, lower alkyl, thienyl, substituted or unsubstituted aryl, hydroxy or amino, or a pharmaceutically acceptable salt thereof.

2. A compound according to claim 1, wherein $R^1$ is hydrogen.

3. A compound according to claim 2, wherein $R^2$ is lower alkyl, thienyl, or substituted or unsubstituted aryl.

4. A compound according to claim 1, wherein said salt is selected from the group consisting of inorganic acid salts and organic acid salts.

5. A pharmaceutical composition comprising a pharmaceutically acceptable carrier and as active ingredient, an effective amount of the compound as defined by claim 1.

* * * * *